(12) United States Patent
Shimokawa et al.

(10) Patent No.: US 11,014,869 B2
(45) Date of Patent: May 25, 2021

(54) METHOD FOR PRODUCING DIALKYL CARBONATE

(71) Applicant: MITSUBISHI GAS CHEMICAL COMPANY, INC., Tokyo (JP)

(72) Inventors: Keisuke Shimokawa, Tokyo (JP); Hidefumi Harada, Tokyo (JP); Takehiko Isobe, Tokyo (JP); Hongyu Liu, Tokyo (JP)

(73) Assignee: MITSUBISHI GAS CHEMICAL COMPANY, INC, Tokyo (JP)

( * ) Notice: Subject to any disclaimer, the term of this patent is extended or adjusted under 35 U.S.C. 154(b) by 0 days.

(21) Appl. No.: 16/639,931

(22) PCT Filed: Aug. 10, 2018

(86) PCT No.: PCT/JP2018/030038
§ 371 (c)(1),
(2) Date: Feb. 18, 2020

(87) PCT Pub. No.: WO2019/039317
PCT Pub. Date: Feb. 28, 2019

(65) Prior Publication Data
US 2020/0239402 A1    Jul. 30, 2020

(30) Foreign Application Priority Data
Aug. 21, 2017  (JP) .............................. JP2017-158713

(51) Int. Cl.
*C07C 68/00* (2020.01)
(52) U.S. Cl.
CPC .................................. *C07C 68/00* (2013.01)
(58) Field of Classification Search
CPC .................................................. C07C 68/00
See application file for complete search history.

(56) References Cited

U.S. PATENT DOCUMENTS

| | | |
|---|---|---|
| 4,327,035 A | 4/1982 | Heitz et al. |
| 4,331,610 A | 5/1982 | Heitz et al. |
| 4,436,668 A | 3/1984 | Harder et al. |
| 6,031,122 A * | 2/2000 | Mizukami ............... C07C 68/00 558/277 |
| 8,921,598 B2 * | 12/2014 | Leitner ................. C07C 271/28 564/135 |
| 2005/0203307 A1 | 9/2005 | Ryu et al. |
| 2007/0082985 A1 | 4/2007 | Buchold et al. |
| 2014/0051880 A1 | 2/2014 | Balk et al. |

FOREIGN PATENT DOCUMENTS

| | | |
|---|---|---|
| JP | 55-102542 | 8/1980 |
| JP | 55-102543 | 8/1980 |
| JP | 57-26645 | 2/1982 |
| JP | 57-175147 | 10/1982 |
| JP | 10-259164 | 9/1998 |
| JP | 2007-534674 | 11/2007 |
| JP | 2014-518553 | 7/2014 |
| WO | 2014/072803 A1 | 5/2014 |

OTHER PUBLICATIONS

Extended European Search Report dated Jul. 9, 2020 in European Patent Application No. 18849278.9.
International Search Report issued in International Patent Application No. PCT/JP2018/030038, dated Oct. 30, 2018.

* cited by examiner

*Primary Examiner* — Golam M Shameem
(74) *Attorney, Agent, or Firm* — Greenblum & Bernstein, P.L.C.

(57) ABSTRACT

The present application addresses the problem of providing a method for efficiently producing a dialkyl carbonate. The problem can be solved by a method for producing a dialkyl carbonate by reacting urea and at least one alkyl carbamate with an aliphatic alcohol in the presence of a catalyst, the method including introducing a gas for expelling ammonia generated by the reaction into a reactor in which the reaction is being conducted and discharging the ammonia generated in the reactor and the introduced gas, the reaction being conducted so that the gas introduction satisfies relationship (1).

$$52.0 < ((A+B) \times 22400 + L \times M/17.03 \times 22400)/L < 91.0 \quad (1)$$

(In formula (1), A, B, L, and M are as defined above.)

9 Claims, 1 Drawing Sheet

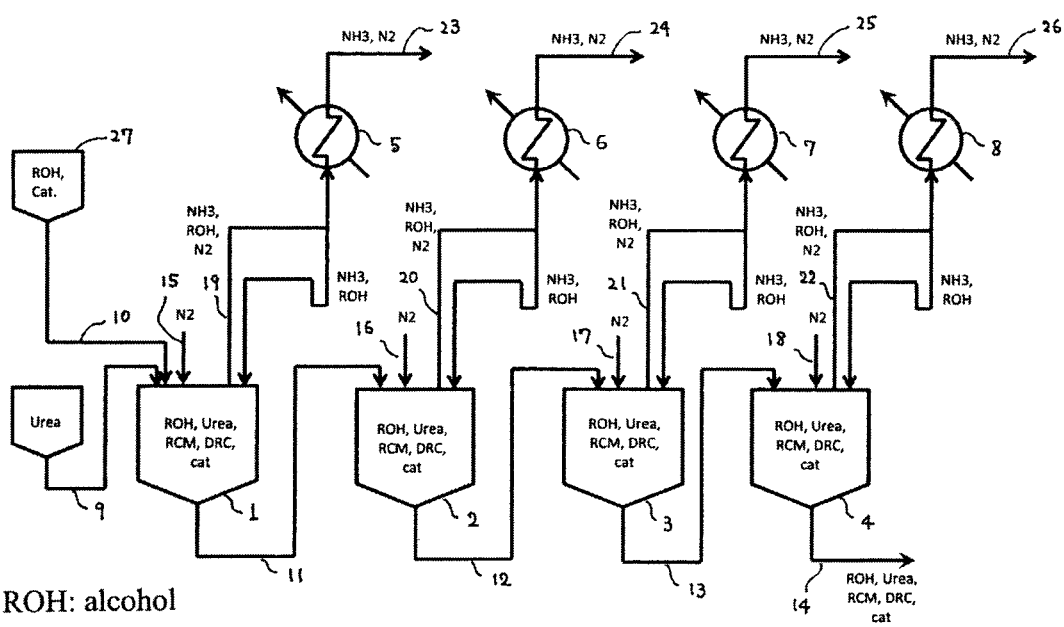
ROH: alcohol
RCM: alkyl carbamate
DRC: dialkyl carbonate

METHOD FOR PRODUCING DIALKYL CARBONATE

TECHNICAL FIELD

The present invention relates to a method for producing a dialkyl carbonate. More specifically, the present invention relates to a method for producing a dialkyl carbonate by reacting urea or an alkyl carbamate with an alcohol in the presence of a catalyst. The dialkyl carbonate is a compound useful as a raw material of a diaryl carbonate, in particular, a diphenyl carbonate.

BACKGROUND ART

A method for producing a dialkyl carbonate by reacting urea with an alcohol is described in Patent Document 1, and a method for producing a dialkyl carbonate by reacting an alkyl carbamate with an alcohol is described in Patent Document 2 and Patent Document 3. Further, catalysts for this reaction are described in Patent Document 4, etc.

Patent Document 5 describes an example in which dibutyl carbonate was produced by using butyl carbamate and butanol as raw materials. According to this method, the reaction was conducted under a pressure of 9 to 10 bar, but the conversion rate of carbamate after 7 hours was only 40%. Further, in the case of using isobutanol, it took 40 hours to complete the reaction, and no practical reaction rate has been obtained.

PRIOR ART DOCUMENTS

Patent Documents

Patent Document 1: Japanese Laid-Open Patent Publication No. S55-102542
Patent Document 2: Japanese Laid-Open Patent Publication No. S55-102543
Patent Document 3: Japanese Laid-Open Patent Publication No. S57-26645
Patent Document 4: Japanese Laid-Open Patent Publication No. S57-175147
Patent Document 5: Japanese Laid-Open Patent Publication No. S57-26645

SUMMARY OF THE INVENTION

Problems to be Solved by the Invention

The present invention addresses the problem of providing a method for efficiently producing a dialkyl carbonate.

Means for Solving the Problems

The present inventors diligently made researches in order to solve the above-described problem and found that it can be solved by the present invention described below.

Specifically, the present invention is as described below.
<1> A method for producing a dialkyl carbonate by reacting urea and at least one alkyl carbamate with an aliphatic alcohol in the presence of a catalyst, the method comprising:
a gas introduction step in which a gas for expelling ammonia generated by the reaction is introduced into a reactor in which the reaction is being conducted; and
a discharge step in which the ammonia generated in the reactor and the introduced gas are simultaneously discharged,
the reaction being conducted so that the gas introduction step satisfies formula (1) below:

$$52.0<((A+B)\times 22400+L\times M/17.03\times 22400)/L<91.0 \quad (1)$$

wherein A, B, L and M are as defined below:
A: an amount of decrease in urea per unit time [mol/min]
B: an amount of increase in the dialkyl carbonate per unit time [mol/min]
L: an amount of the aliphatic alcohol contained in a liquid condensed in a condenser tube and refluxed to the reactor per unit time [g/min]
M: the solubility of ammonia in the aliphatic alcohol (ROH) at a condenser tube temperature and under a pressure condition at the time of conducting the reaction [$NH_3$-g/ROH-g]
<2> The method according to item <1>, wherein the dialkyl carbonate has an alkyl group having 1 to 6 carbon atoms.
<3> The method according to item <1> or <2>, wherein the gas contains 21% or less of oxygen.
<4> The method according to item <1> or <2>, wherein the gas is an inert gas.
<5> The method according to item <4>, wherein the inert gas is nitrogen or argon.
<6> The method according to any one of items <1> to <5>, wherein: as the reactor, a multistage reactor in which two or more reactors are arranged in series is used; the gas is introduced into each of the reactors; and the generated ammonia and the introduced gas are simultaneously discharged.

Advantageous Effect of the Invention

According to the present invention, it is possible to provide a method for efficiently producing a dialkyl carbonate.

BRIEF DESCRIPTION OF THE DRAWINGS

FIG. 1 shows one example of a continuous reactor for dialkyl carbonate preferably used in the present invention.

EMBODIMENTS FOR CARRYING OUT THE INVENTION

Hereinafter, the present invention will be described in detail.

The present invention relates to a method for producing a dialkyl carbonate by reacting urea and at least one alkyl carbamate with an aliphatic alcohol in the presence of a catalyst, wherein the method includes: a gas introduction step in which a gas for expelling ammonia generated by the reaction is introduced into a reactor in which the reaction is conducted; and a discharge step in which the ammonia generated in the reactor and the introduced gas are simultaneously discharged.

The alkyl group of the dialkyl carbonate to be produced in the present invention is preferably an alkyl group having 1 to 6 carbon atoms, and more preferably an alkyl group having 2 to 4 carbon atoms.

The aliphatic alcohol to be used in the present invention is not particularly limited, but usually, an aliphatic alcohol having 1 to 8 carbon atoms is used. Examples of these aliphatic alcohols include methanol, ethanol, propanol, butanol, pentanol, cyclopentanol, hexanol, cyclohexanol, heptanol and octanol (respective examples include isomers thereof). Among these aliphatic alcohols, an aliphatic alcohol having 2 to 6 carbon atoms is preferably used, an aliphatic alcohol having 3 to 6 carbon atoms is more preferably used, and an aliphatic alcohol having 3 to 5 carbon atoms is particularly preferably used because the effect of improving the reaction rate is significant. An aliphatic alcohol having 3 or 4 carbon atoms is most preferred.

The alkyl carbamate to be used in the present invention is an alkyl carbamate obtained by reacting urea with the above-described aliphatic alcohol and is an intermediate product of the production method of the present invention. In the present invention, a reaction from urea to the alkyl carbamate and a reaction from the alkyl carbamate to the dialkyl carbonate occur serially in the same reactor, and for this reason, it is not particularly necessary to take out the alkyl carbamate as the intermediate. Conversely, there is no problem when the alkyl carbamate is used as a raw material. Accordingly, in the present invention, the alkyl carbamate collected in a separation process can be reused as a raw material.

As the catalyst to be used in the present invention, publicly-known catalysts can be used. As catalysts for this reaction, many catalysts have already been reported, for example, in Japanese Laid-Open Patent Publication Nos. S55-102542, S55-102543, S57-26645 and S57-175147, and any of these catalysts can be used in the present invention. Among them, an oxide, hydroxide, halide, inorganic salt, organic salt, alkoxide, alkyloxide or alkylalkoxide of at least one metal selected from zinc, lead, copper, tin, titanium, gallium and indium is particularly preferably used. Specific examples thereof include zinc oxide, lead acetate, copper acetate, dibutyl tin oxide, dioctyl tin oxide, dibutyldibutoxytin, tetrabutoxytitanium and gallium tributoxide.

The reaction may be performed under atmospheric pressure, but it is preferably performed under reduced pressure or elevated pressure with an absolute pressure of about 0.001 to 1.0 MPa, and more preferably with an absolute pressure of 0.001 to 0.5 MPa. When the reaction is performed under a pressure other than atmospheric pressure, it is required to expel ammonia generated during the reaction to the outside of the system. For this reason, for example, a pressure regulator is required to be arranged next to a reflux condenser, resulting in a somewhat complicated apparatus.

The gas to be used in the gas introduction step in the present invention is not particularly limited as long as it can expel ammonia generated by the reaction, but from the viewpoint of explosion-proof, it is preferred that the gas contains 21% or less of oxygen, it is more preferred that the gas contains 10% or less, 5% or less, 1% or less or 0.1% or less of oxygen, and it is particularly preferred that the gas contains 0.01% or less of oxygen. The aforementioned gas is more preferably an inert gas, and among inert gases, nitrogen and argon are particularly preferred.

The amount of the gas to be introduced is preferably 0.01 to 300 mL/min, more preferably 0.01 to 50 mL/min, even more preferably 1 to 50 mL/min, and particularly preferably 10 to 50 mL/min per 1 mol (amount of substance) of a reactant (urea+alkyl carbamate). When the amount is within the above-described range, ammonia generated by the reaction can be efficiently expelled.

The present invention is characterized in that the reaction is conducted so that the gas introduction step satisfies formula (1) below:

$$52.0 < ((A+B) \times 22400 + L \times M/17.03 \times 22400)/L < 91.0 \qquad (1)$$

wherein A, B, L and M are as defined below:
A: an amount of decrease in urea per unit time [mol/min]
B: an amount of increase in the dialkyl carbonate per unit time [mol/min]
L: an amount of the aliphatic alcohol contained in a liquid condensed in a condenser tube and refluxed to the reactor per unit time [g/min]
M: the solubility of ammonia in the aliphatic alcohol (ROH) at a condenser tube temperature and under a pressure condition at the time of conducting the reaction [$NH_3$-g/ROH-g]

By conducting the reaction so that the gas introduction step satisfies formula (1) above, the dialkyl carbonate can be efficiently produced.

The reaction is conducted so that the gas introduction step satisfies preferably $54.0 < ((A+B) \times 22400 + L \times M/17.03 \times 22400)/L < 86.0$, more preferably $56.0 < ((A+B) \times 22400 + L \times M/17.03 \times 22400)/L < 83.0$, and particularly preferably $56.0 < ((A+B) \times 22400 + L \times M/17.03 \times 22400)/L < 60.0$.

The present invention is also characterized in that it has a discharge step in which the ammonia generated in the reactor and the introduced gas are simultaneously discharged.

For facilitating discharge of the generated ammonia, the reaction is preferably conducted in a state where the reaction solution is refluxed. Specifically, the reaction temperature is preferably the boiling point of the reaction solution. As the reaction proceeds, the boiling point of the reaction solution is increased by consumption of the aliphatic alcohol. The reaction may be conducted by feeding an appropriate amount of the aliphatic alcohol at first with the solution temperature being left. Alternatively, the reaction may be continuously conducted while maintaining the boiling point of the reaction solution at an appropriate temperature by suitably adding the aliphatic alcohol. The reaction temperature is appropriately set at about 140 to 260° C., preferably 160 to 240° C., and more preferably 200 to 220° C. The retention time of the reaction is appropriately set at 1 to 20 hours, and usually 2 to 10 hours. Note that it is not necessarily required to complete the reaction because the alkyl carbamate as the intermediate can be collected and used as the raw material.

The appropriate amount of the aliphatic alcohol to be added (the total amount of the aliphatic alcohol added to the respective reactors) is 1 to 3 mol relative to 1 mol of urea. When the alkyl carbamate is contained in the raw material, it is preferred to further add the aliphatic alcohol in an amount of 0.5 to 1.5 mol relative to 1 mol of carbamate. The total amount of the aliphatic alcohol may be introduced into the first reactor. However, since the aliphatic alcohol has the lowest boiling point among reactants, when a large amount of the aliphatic alcohol is put into the reactor from the start, the boiling point of the whole reaction solution is reduced. That is, the reaction temperature is decreased and the reaction rate is reduced. Accordingly, the aliphatic alcohol may be added to the respective reactors depending on the reaction progress. In the present invention, it is preferred to introduce the total amount of the aliphatic alcohol into the first reactor since the reaction process is not complicated in this case.

The amount of the catalyst varies depending on the type of the catalyst to be used, but the appropriate amount is usually about 0.001 to 0.5 mol relative to 1 mol of urea.

The present invention is more preferably a method for continuously producing a dialkyl carbonate, though a batch method can also be employed. The dialkyl carbonate can be produced by a batch reaction, or more preferably a semi-batch reaction in which the aliphatic alcohol is added depending on the degree of the reaction. However, in this case, a very large reactor is required and it may be not practical. Meanwhile, when a multistage reactor is used, mixing of a reaction solution whose conversion rate is increased and an unreacted raw material can be avoided, and for this reason, the dialkyl carbonate can be efficiently produced by combining relatively small reactors.

In the present invention, a high boiling point solvent may be used.

The reaction solution is continuously drawn from the bottom reactor and separation operation is carried out. As the separation method, distillation is usually employed. The reaction solution contains the aliphatic alcohol as the raw material, the alkyl carbamate as the intermediate and the catalyst in addition to the dialkyl carbonate as the product. A solution obtained after the dialkyl carbonate is separated is circulated to the reaction system. That is, the catalyst is reused, and the aliphatic alcohol and the alkyl carbamate are used as raw materials.

As the reactor to be used in the present invention, a continuous multistage reactor is preferably used. In general, a tank-type or column-type reactor is used, and the number of stages of the reactor is required to be 2 or more, and preferably 3 or more. When using a tank-type reactor, it is required to arrange a reflux condenser or a distillation column above the reactor and to separate the aliphatic alcohol and ammonia. Note that when the present invention is carried out using a batch system, a batch-type reactor can be used.

Next, the production of the dialkyl carbonate from the aliphatic alcohol and urea will be explained, showing one example of a continuous reactor for dialkyl carbonate preferably used in the present invention in FIG. 1.

In FIG. 1, 4 reactors are arranged in series. In the FIGURE, 1, 2, 3 and 4 are stirring tank-type reactors, and 5, 6, 7 and 8 are reflux condensers. Urea is continuously introduced from a urea introduction tube 9, and the aliphatic alcohol and the catalyst are introduced into the reactor 1 from an alcohol and catalyst introduction tube 10 according to need. In this regard, the aliphatic alcohol and the catalyst may be homogeneously mixed in a preliminary mixing tank 27, and after that, the mixture may be continuously delivered to the stirring tank-type reactor 1 through the alcohol and catalyst introduction tube 10. In the gas introduction step, a gas for expelling ammonia generated in the reactor 1 is introduced into the reactor 1 from a gas introduction valve 15. In the discharge step, the ammonia generated in the reactor 1 and the introduced gas are passed through a distillation tube 19 and simultaneously discharged from a back pressure valve 23.

In the respective reactors, the reaction is conducted while the reaction solution is refluxed. From the respective reactors, a mixed steam of ammonia and the aliphatic alcohol is generated. The aliphatic alcohol is returned to the reactor 1 via the reflux condenser 5, and ammonia is passed through the reflux condenser 5 and discharged from the back pressure valve 23 that is arranged after the reflux condenser 5 and an ammonia and gas drawing tube 23 arranged next thereto. The reaction solution of the reactor 1 is continuously supplied to the reactor 2 via a reaction solution drawing tube 11. As the supply method, either an overflow style or liquid delivery using a pump may be employed. However, in the case of the overflow style, it is required to devise a method in which steam generated in the reactor 2 does not return to the reactor 1 (e.g., an introduction tube is inserted below the liquid level). Also in the reactor 2, the reaction is conducted while the reaction solution is refluxed. During this, the aliphatic alcohol may be additionally supplied according to need. The reaction solution of the reactor 2 is continuously supplied to the reactor 3 via a reaction solution drawing tube 12. Also in the reactor 3, the reaction is conducted while the reaction solution is refluxed. During this, the aliphatic alcohol may be additionally supplied according to need. The reaction solution of the reactor 4 is continuously drawn via a reaction solution drawing tube 14 and sent to the separation process.

The reaction tank is not necessarily required to be equipped with a stirring apparatus, and it may be in a form in which stirring is carried out by outside circulation or the like. Capacities of respective reactors are not required to be uniform. The reflux condenser can be replaced by a distillation column. It is possible to employ a method in which steam generated is treated with one reflux condenser, for example, a method in which whole steam generated in the reactor 2 and the reactor 3 is condensed by the reflux condenser 5 and returned to the reactor 1, but it is not preferred because the concentration of the aliphatic alcohol in the respective reactors cannot be maintained. Note that it is preferred if an apparatus which can appropriately distribute collected steam to the respective reactors is provided.

In the reaction, by-products including ammonium cyanate and ammonium carbonate are produced though amounts thereof are very small, and these compounds may close a pipe arrangement in the case of operation for a long period of time. Since the dissociation temperature of these compounds under ordinary pressure is about 60° C., it is preferred to keep the temperature of the pipe arrangement to which the compounds may adhere at the dissociation temperature or higher. Further, the reflux condenser is preferably operated under a pressure that is equal to or more than the dissociation pressure of these salts (60° C. or higher under ordinary pressure) and at a temperature that is equal to or lower than the boiling point of the aliphatic alcohol to be used.

As the column-type reactor, an ordinary multistage distillation column can be directly used as the reactor. The form of the distillation column is not particularly limited, but a tray column-type distillation column is preferred because the retention time is required. Specifically, a tray column in which a bubble cap tray, a perforated tray, a valve tray or the like is used is preferred. When using the column-type reactor, urea, the aliphatic alcohol and the catalyst are continuously supplied to the upper portion or center portion of the tray column, and gaseous ammonia is continuously drawn from the top of the distillation column while the reaction solution is continuously drawn from the bottom of the column, thereby conducting the reaction. Moreover, in this case, it is preferred that a mixture of urea and the catalyst is continuously supplied to the upper portion or center portion of the tray column, and that the aliphatic alcohol is supplied from the tray to which the above-described mixture is supplied and a plurality of optional trays below the tray.

EXAMPLES

Hereinafter, the present invention will be specifically described by way of working examples, but the present invention is not limited thereto.

Example 1-A

The experiment was conducted using a stirring machine and a stainless steel stirring tank-type reactor 1 having a reflux condenser 5 above. As an alcohol, n-butanol was used, and as a catalyst, dibutyl tin oxide was used. A solution containing 260.5 g of n-butanol, 373.3 g of butyl carbamate, 192.1 g of dibutyl carbonate and 18.9 g of the catalyst relative to 18.2 g of urea was homogeneously mixed in a preliminary mixing tank 27 equipped with a steam jacket, and after that, the solution was continuously delivered to the stirring tank-type reactor 1 at a rate of 863.0 g/h. The temperature of the stirring tank-type reactor 1 was set at 209.2° C. Hot water (80° C.) was flowed through the reflux condenser 5. Nitrogen was introduced into the system from a gas introduction valve 15 at a rate of 50 mL/min while it was discharged from a back pressure valve 23 via a distillation tube 19. Ammonia generated in the stirring tank-type reactor 1 was separated from butanol by the reflux condenser 5 and then discharged to the outside of the system from the back pressure valve 23 that was arranged after the reflux condenser 5 and an ammonia and gas drawing tube 23 arranged next thereto.

Comparative Example 1

The experiment was conducted in a manner similar to that in Example 1-A, except that: the composition of a raw material solution was adjusted in a manner such that 267.8 g of n-butanol, 368.9 g of butyl carbamate, 190.4 g of dibutyl carbonate and 18.9 g of the catalyst were contained relative to 24.5 g of urea and the solution was delivered to the stirring tank-type reactor at a rate of 870.5 g/h; the temperature of the stirring tank-type reactor was set at 208.8° C.; and nitrogen was not introduced into the system.

Example 2-A

The experiment was conducted in a manner similar to that in Example 1-A, except that: the composition of a raw material solution was adjusted in a manner such that 146.8 g of n-butanol, 49.5 g of dibutyl carbonate and 4.7 g of the catalyst were contained relative to 129.2 g of butyl carbamate and the solution was delivered to the stirring tank-type reactor at a rate of 327.0 g/h; the temperature of the stirring tank-type reactor was set at 212.3° C.; and nitrogen was introduced into the system at a rate of 150 mL/min while it was discharged from the back pressure valve.

Example 2-B

The experiment was conducted in a manner similar to that in Example 1-A, except that: the composition of a raw material solution was adjusted in a manner such that 148.4 g of n-butanol, 50.9 g of dibutyl carbonate and 4.7 g of the catalyst were contained relative to 123.1 g of butyl carbamate and the solution was delivered to the stirring tank-type reactor at a rate of 330.1 g/h; the temperature of the stirring tank-type reactor was set at 213.2° C.; and nitrogen was introduced into the system at a rate of 50 mL/min while it was discharged from the back pressure valve.

Example 2-C

The experiment was conducted in a manner similar to that in Example 1-A, except that: the composition of a raw material solution was adjusted in a manner such that 151.6 g of n-butanol, 49.3 g of dibutyl carbonate and 4.7 g of the catalyst were contained relative to 118.2 g of butyl carbamate and the solution was delivered to the stirring tank-type reactor at a rate of 323.7 g/h; the temperature of the stirring tank-type reactor was set at 212.0° C.; and nitrogen was introduced into the system at a rate of 10 mL/min while it was discharged from the back pressure valve.

Comparative Example 2

The experiment was conducted in a manner similar to that in Example 1-A, except that: the composition of a raw material solution was adjusted in a manner such that 153.3 g of n-butanol, 47.0 g of dibutyl carbonate and 4.7 g of the catalyst were contained relative to 119.8 g of butyl carbamate and the solution was delivered to the stirring tank-type reactor at a rate of 324.8 g/h; the temperature of the stirring tank-type reactor was set at 210.8° C.; and nitrogen was not introduced into the system.

Example 3-A

The experiment was conducted in a manner similar to that in Example 1-A, except that: the composition of a raw material solution was adjusted in a manner such that 121.8 g of n-butanol, 107.6 g of dibutyl carbonate and 4.7 g of the catalyst were contained relative to 84.9 g of butyl carbamate and the solution was delivered to the stirring tank-type reactor at a rate of 327.5 g/h; the temperature of the stirring tank-type reactor was set at 215.1° C.; and nitrogen was introduced into the system at a rate of 50 mL/min while it was discharged from the back pressure valve.

Example 3-B

The experiment was conducted in a manner similar to that in Example 1-A, except that: the composition of a raw material solution was adjusted in a manner such that 125.0 g of n-butanol, 108.9 g of dibutyl carbonate and 4.7 g of the catalyst were contained relative to 78.5 g of butyl carbamate and the solution was delivered to the stirring tank-type reactor at a rate of 317.1 g/h; the temperature of the stirring tank-type reactor was set at 214.4° C.; and nitrogen was introduced into the system at a rate of 10 mL/min while it was discharged from the back pressure valve.

Comparative Example 3

The experiment was conducted in a manner similar to that in Example 1-A, except that: the composition of a raw material solution was adjusted in a manner such that 128.0 g of n-butanol, 98.2 g of dibutyl carbonate and 4.7 g of the catalyst were contained relative to 82.5 g of butyl carbamate and the solution was delivered to the stirring tank-type reactor at a rate of 313.3 g/h; the temperature of the stirring tank-type reactor was set at 213.3° C.; and nitrogen was not introduced into the system.

Comparative Example 4-A

The experiment was conducted in a manner similar to that in Example 1-A, except that: the composition of a raw material solution was adjusted in a manner such that 680.5 g of n-butanol and 18.9 g of the catalyst were contained relative to 275.7 g of urea and the solution was delivered to the stirring tank-type reactor at a rate of 975.1 g/h; the temperature of the stirring tank-type reactor was set at 197.6° C.; and nitrogen was introduced into the system at a rate of 50 mL/min while it was discharged from the back pressure valve.

Comparative Example 4-B

The experiment was conducted in a manner similar to that in Example 1-A, except that: the composition of a raw material solution was adjusted in a manner such that 680.5 g of n-butanol and 18.9 g of the catalyst were contained relative to 275.7 g of urea and the solution was delivered to the stirring tank-type reactor at a rate of 975.1 g/h; the temperature of the stirring tank-type reactor was set at 192.4° C.; and nitrogen was not introduced into the system.

Comparative Example 5-A

The experiment was conducted in a manner similar to that in Example 1-A, except that: the composition of a raw material solution was adjusted in a manner such that 346.7 g of n-butanol, 476.0 g of butyl carbamate, 17.8 g of dibutyl carbonate and 18.9 g of the catalyst were contained relative to 28.4 g of urea and the solution was delivered to the stirring tank-type reactor at a rate of 887.8 g/h; the temperature of the stirring tank-type reactor was set at 206.2° C.; and nitrogen was introduced into the system at a rate of 50 mL/min while it was discharged from the back pressure valve.

Comparative Example 5-B

The experiment was conducted in a manner similar to that in Example 1-A, except that: the composition of a raw material solution was adjusted in a manner such that 375.3 g of n-butanol, 461.6 g of butyl carbamate, 10.8 g of dibutyl carbonate and 18.9 g of the catalyst were contained relative to 35.3 g of urea and the solution was delivered to the stirring tank-type reactor at a rate of 901.9 g/h; the temperature of the stirring tank-type reactor was set at 207.5° C.; and nitrogen was not introduced into the system.

Comparative Example 6-A

The experiment was conducted in a manner similar to that in Example 1-A, except that: the composition of a raw material solution was adjusted in a manner such that 84.9 g of n-butanol, 198.0 g of dibutyl carbonate and 4.7 g of the catalyst were contained relative to 39.9 g of butyl carbamate and the solution was delivered to the stirring tank-type reactor at a rate of 327.5 g/h; the temperature of the stirring tank-type reactor was set at 216.2° C.; and nitrogen was introduced into the system at a rate of 50 mL/min while it was discharged from the back pressure valve.

Comparative Example 6-B

The experiment was conducted in a manner similar to that in Example 1-A, except that: the composition of a raw material solution was adjusted in a manner such that 99.6 g of n-butanol, 176.9 g of dibutyl carbonate and 4.7 g of the catalyst were contained relative to 43.3 g of butyl carbamate and the solution was delivered to the stirring tank-type reactor at a rate of 324.6 g/h; the temperature of the stirring tank-type reactor was set at 215.5° C.; and nitrogen was not introduced into the system.

The conditions and yields of dibutyl carbonates obtained in Examples 1-3 and Comparative Examples 1-6 are shown in Tables 1 and 2 below.

TABLE 1

| | Reaction solution temperature ° C. | Pressure MPaG | Composition for feeding | | | | | Composition of reaction solution |
| --- | --- | --- | --- | --- | --- | --- | --- | --- |
| | | | Urea g | Butanol g | Butyl carbamate g | Dibutyl carbonate g | $Bu_2SnO$ g | Urea g |
| Example 1-A | 209.2 | 0.4 | 18.2 | 260.5 | 373.3 | 192.1 | 18.9 | 16.0 |
| Comparative Example 1 | 208.8 | 0.4 | 24.5 | 267.8 | 368.9 | 190.4 | 18.9 | 23.7 |
| Example 2-A | 212.3 | 0.3 | 0 | 146.8 | 129.2 | 49.5 | 4.7 | 0 |
| Example 2-B | 213.2 | 0.3 | 0 | 148.4 | 123.1 | 50.9 | 4.7 | 0 |
| Example 2-C | 212.0 | 0.3 | 0 | 151.6 | 118.2 | 49.3 | 4.7 | 0 |
| Comparative Example 2 | 210.8 | 0.3 | 0 | 153.3 | 119.8 | 47.0 | 4.7 | 0 |
| Example 3-A | 215.1 | 0.3 | 0 | 121.8 | 84.9 | 107.6 | 4.7 | 0 |
| Fxnmple 3-B | 214.4 | 0.3 | 0 | 125.0 | 78.5 | 108.9 | 4.7 | 0 |
| Comparative Example 3 | 213.3 | 0.3 | 0 | 128.0 | 82.5 | 98.2 | 4.7 | 0 |
| Comparative Example 4-A | 197.6 | 0.4 | 275.7 | 680.5 | 0 | 0 | 18.9 | 28.4 |
| Comparative Example 4-B | 192.4 | 0.4 | 275.7 | 680.5 | 0 | 0 | 18.9 | 35.3 |
| Comparative Example 5-A | 206.2 | 0.4 | 28.4 | 346.7 | 476.0 | 17.8 | 18.9 | 18.2 |
| Comparative Example 5-B | 207.5 | 0.4 | 35.3 | 375.3 | 461.6 | 10.8 | 18.9 | 24.5 |
| Comparative Example 6-A | 216.2 | 0.3 | 0 | 84.9 | 39.9 | 198.0 | 4.7 | 0 |
| Comparative Example 6-B | 215.5 | 0.3 | 0 | 99.6 | 43.3 | 176.9 | 4.7 | 0 |

| | Composition of reaction solution | | | Amount of refluxed liquid g/h | Composition of refluxed liquid | | |
| --- | --- | --- | --- | --- | --- | --- | --- |
| | Butanol g | Butyl carbamate g | Dibutyl carbonate g | | Butanol g/h | Butyl carbamate g/h | Dibutyl carbonate g/h |
| Example 1-A | 230.2 | 325.4 | 263.0 | 582 | 556.2 | 16.9 | 9.3 |
| Comparative Example 1 | 235.5 | 335.6 | 232.0 | 579 | 553.4 | 16.8 | 9.3 |

TABLE 1-continued

|  | | | | | | | |
|---|---|---|---|---|---|---|---|
| Example 2-A | 116.4 | 87.0 | 111.5 | 873 | 704 | 58 | 73 |
| Example 2-B | 121.8 | 84.9 | 107.6 | 882 | 711 | 58 | 74 |
| Example 2-C | 125.0 | 78.5 | 108.9 | 901 | 726 | 60 | 76 |
| Comparative Example 2 | 128.0 | 82.5 | 98.2 | 911 | 735 | 60 | 76 |
| Example 3-A | 104.5 | 60.1 | 141.2 | 633 | 493 | 46 | 76 |
| Example 3-B | 110.5 | 54.9 | 140.8 | 649 | 506 | 47 | 78 |
| Comparative Example 3 | 118.3 | 63.6 | 126.2 | 664 | 518 | 49 | 80 |
| Comparative Example 4-A | 346.7 | 476.0 | 17.8 | 1539 | 1469.7 | 44.6 | 24.6 |
| Comparative Example 4-B | 375.3 | 461.6 | 10.8 | 1539 | 1469.7 | 44.6 | 24.6 |
| Comparative Example 5-A | 260.5 | 373.3 | 192.1 | 659 | 629.3 | 19.1 | 10.5 |
| Comparative Example 5-B | 267.8 | 368.9 | 190.4 | 659 | 629.3 | 19.1 | 10.5 |
| Comparative Example 6-A | 83 | 38 | 201 | 522 | 391 | 37 | 78 |
| Comparative Example 6-B | 98 | 41 | 180 | 589 | 448 | 42 | 82 |

TABLE 2

|  | Discharge amount of ammonia per g/h of butanol in reaction solution mL/min · BuOH-g/min | Flow rate of $N_2$ mL/min | Yield of dibutyl carbonate (yield per unit time) mol %/h | A: Amount of decrease in urea per unit time mol/min | B: Amount of increase in dialkyl carbonate per unit time mol/min |
|---|---|---|---|---|---|
| Example 1-A | 0.70 | 50 | 8.9 | 0.00061 | 0.00678 |
| Comparative Example 1 | 0.26 | 0 | 5.2 | 0.00023 | 0.00398 |
| Example 2-A | 0.57 | 150 | 13.8 | 0.00000 | 0.00297 |
| Example 2-B | 0.50 | 50 | 12.8 | 0.00000 | 0.00271 |
| Example 2-C | 0.51 | 10 | 13.3 | 0.00000 | 0.00285 |
| Comparative Example 2 | 0.43 | 0 | 0.2 | 0.00000 | 0.00245 |
| Example 3-A | 0.34 | 50 | 9.2 | 0.00000 | 0.00160 |
| Example 3-B | 0.31 | 10 | 8.9 | 0.00000 | 0.00152 |
| Comparative Example 3 | 0.25 | 0 | 0.1 | 0.00000 | 0.00134 |
| Comparative Example 4-A | 4.59 | 50 | 2.2 | 0.06863 | 0.00170 |
| Comparative Example 4-B | 4.04 | 0 | 2.1 | 0.06671 | 0.00103 |
| Comparative Example 5-A | 0.81 | 50 | 10.9 | 0.00283 | 0.00834 |
| Comparative Example 5-B | 0.95 | 0 | 10.8 | 0.00299 | 0.00859 |
| Comparative Example 6-A | 0.04 | 50 | 1.28 | 0.00000 | 0.00016 |
| Comparative Example 6-B | 0.03 | 0 | 1.25 | 0.00000 | 0.00015 |

|  | M: Solubility of ammonia in aliphatic alcohol (ROH) at condenser tube temperature and under pressure condition at the time of conducting reaction $NH_3$-g/ROH-g | L: Amount of aliphatic alcohol contained in liquid condensed in condenser tube and refluxed to reactor per unit time g/min | Calculation formula (1) ((A + B) × 22400 + L × M/17.03 × 22400)/L |
|---|---|---|---|
| Example 1-A | 0.0516 | 9.3 | 85.7 |
| Comparative Example 1 | 0.0516 | 9.2 | 78.1 |
| Example 2-A | 0.0387 | 11.7 | 56.6 |
| Example 2-B | 0.0387 | 11.9 | 56.0 |
| Example 2-C | 0.0387 | 12.1 | 56.2 |
| Comparative Example 2 | 0.0387 | 12.2 | 55.4 |

TABLE 2-continued

| | | | |
|---|---|---|---|
| Example 3-A | 0.0387 | 8.2 | 55.3 |
| Example 3-B | 0.0387 | 8.4 | 54.9 |
| Comparative Example 3 | 0.0387 | 8.6 | 54.4 |
| Comparative Example 4-A | 0.0516 | 24.5 | 132.2 |
| Comparative Example 4-B | 0.0516 | 24.5 | 129.8 |
| Comparative Example 5-A | 0.0516 | 10.5 | 91.7 |
| Comparative Example 5-B | 0.0516 | 10.5 | 92.6 |
| Comparative Example 6-A | 0.0387 | 6.5 | 51.5 |
| Comparative Example 6-B | 0.0387 | 7.5 | 51.4 |

INDUSTRIAL APPLICABILITY

According to the present invention, a dialkyl carbonate can be efficiently produced, and the dialkyl carbonate obtained is a compound useful as a raw material of a diaryl carbonate, in particular, a diphenyl carbonate.

EXPLANATIONS OF LETTERS OR NUMERALS 1 stirring tank-type reactor
2 stirring tank-type reactor
3 stirring tank-type reactor
4 stirring tank-type reactor
5 reflux condenser
6 reflux condenser
7 reflux condenser
8 reflux condenser
9 urea introduction tube
10 alcohol and catalyst introduction tube
11 reaction solution drawing tube
12 reaction solution drawing tube
13 reaction solution drawing tube
14 reaction solution drawing tube
15 gas introduction valve
16 gas introduction valve
17 gas introduction valve
18 gas introduction valve
19 distillation tube
20 distillation tube
21 distillation tube
22 distillation tube
23 back pressure valve, ammonia and gas drawing tube
24 back pressure valve, ammonia and gas drawing tube
25 back pressure valve, ammonia and gas drawing tube
26 back pressure valve, ammonia and gas drawing tube
27 preliminary mixing tank

The invention claimed is:

1. A method for producing a dialkyl carbonate by reaction of at least one of urea and alkyl carbamate with an aliphatic alcohol in the presence of a catalyst that catalyzes said reaction, wherein the catalyst is present in an amount sufficient to catalyze said reaction, the method comprising:
   introducing into a reactor in which the reaction is occurring a gas for expelling ammonia generated by the reaction; and
   simultaneously discharging the ammonia generated in the reactor and the gas for expelling ammonia, wherein the reaction and gas introduction satisfies formula (1) below:

$$52.0 < ((A+B) \times 22400 + L \times M/17.03 \times 22400)/L < 91.0 \quad (1)$$

wherein A, B, L, and M are as defined below:
A: an amount of decrease in urea per unit time [mol/min]
B: an amount of increase in the dialkyl carbonate per unit time [mol/min]
L: an amount of the aliphatic alcohol contained in a liquid condensed in a condenser tube and refluxed to the reactor per unit time [g/min]
M: the solubility of ammonia in the aliphatic alcohol (ROH) at a condenser tube temperature and under a pressure condition at the time of conducting the reaction [$NH_3$-g/ROH-g].

2. The method according to claim 1, wherein the dialkyl carbonate has an alkyl group having 1 to 6 carbon atoms.

3. The method according to claim 1, wherein the gas contains 21% or less of oxygen.

4. The method according to claim 1, wherein the gas is an inert gas.

5. The method according to claim 4, wherein the inert gas is nitrogen or argon.

6. The method according to claim 1, wherein: as the reactor, a multistage reactor in which two or more reactors are arranged in series is used; the gas is introduced into each of the reactors; and the generated ammonia and the introduced gas are simultaneously discharged.

7. The method according to claim 1, wherein the catalyst is selected from the group consisting of an oxide, hydroxide, halide, inorganic salt, organic salt, alkoxide, alkyloxide, and alkylalkoxide of at least one metal selected from the group consisting of zinc, lead, copper, tin, titanium, gallium, and indium.

8. The method according to claim 7, wherein the catalyst is selected from the group consisting of zinc oxide, lead acetate, copper acetate, dibutyl tin oxide, dioctyl tin oxide, dibutyldibutoxytin, tetrabutoxytitanium, and gallium tributoxide.

9. The method according to claim 1, wherein an amount of the catalyst is about 0.001 to 0.5 mol relative to 1 mol of urea.

* * * * *